United States Patent
Cooper et al.

(10) Patent No.: US 9,756,862 B2
(45) Date of Patent: Sep. 12, 2017

(54) PROPORTIONER-READY BIOENZYMATIC CONCENTRATED CLEANING PRODUCT

(75) Inventors: Donald A. Cooper, Centerville, MD (US); Jonathan A. Long, Bethel, DE (US)

(73) Assignee: Illinois Tool Works Inc., Glenview, IL (US)

( * ) Notice: Subject to any disclaimer, the term of this patent is extended or adjusted under 35 U.S.C. 154(b) by 406 days.

(21) Appl. No.: 13/533,029

(22) Filed: Jun. 26, 2012

(65) Prior Publication Data

US 2013/0053294 A1 Feb. 28, 2013

Related U.S. Application Data

(60) Provisional application No. 61/526,797, filed on Aug. 24, 2011.

(51) Int. Cl.
| | | |
|---|---|---|
| *C11D 3/38* | (2006.01) | |
| *C11D 11/00* | (2006.01) | |
| *A01N 63/00* | (2006.01) | |
| *A61L 11/00* | (2006.01) | |
| *C12N 1/20* | (2006.01) | |
| *C12N 3/00* | (2006.01) | |

(52) U.S. Cl.
CPC .............. *A01N 63/00* (2013.01); *A61L 11/00* (2013.01); *C12N 1/20* (2013.01); *C12N 3/00* (2013.01)

(58) Field of Classification Search
CPC ... C11D 3/0031; C11D 3/381; C11D 11/0094; A61L 11/00; C12N 1/20; C12N 3/00; A01N 63/00
USPC ..... 510/195, 238, 280, 337, 434; 435/252.5, 435/263, 264
See application file for complete search history.

(56) References Cited

U.S. PATENT DOCUMENTS

| | | | | |
|---|---|---|---|---|
| 3,271,243 | A * | 9/1966 | Cords et al. ............. | 424/93.461 |
| 3,506,582 | A * | 4/1970 | Gertzman ................... | 510/195 |
| 3,532,599 | A * | 10/1970 | Cooperman ....... | C11D 3/38618 101/424 |
| 3,746,649 | A * | 7/1973 | Barrett, Jr. ......... | C11D 17/0043 435/188 |
| 3,844,890 | A * | 10/1974 | Horikoshi ........ | C12Y 302/0100 435/209 |
| 5,312,561 | A * | 5/1994 | Hoshino et al. .............. | 510/320 |
| 5,447,575 | A * | 9/1995 | Crump .................. | C07C 309/14 134/22.14 |
| 5,863,882 | A * | 1/1999 | Lin et al. ....................... | 510/397 |
| 6,165,965 | A * | 12/2000 | Schalitz et al. .............. | 510/384 |
| 6,180,585 | B1 * | 1/2001 | Schalitz et al. .............. | 510/384 |
| 6,387,874 | B1 * | 5/2002 | Schalitz et al. .............. | 510/530 |
| 6,448,062 | B1 * | 9/2002 | Huth ......................... | A61L 2/18 435/264 |
| 6,498,137 | B1 * | 12/2002 | Schalitz et al. .............. | 510/530 |
| 6,929,702 | B1 * | 8/2005 | Motsenbocker ......... | C11D 3/43 134/40 |
| 2005/0020466 | A1 * | 1/2005 | Man .................... | C11D 3/38663 510/392 |
| 2005/0227893 | A1 * | 10/2005 | Johnson ............... | C11D 3/0031 510/367 |
| 2006/0247150 | A1 * | 11/2006 | Molinaro et al. ............ | 510/499 |
| 2006/0293212 | A1 * | 12/2006 | Griese et al. ................. | 510/446 |
| 2009/0324533 | A1 * | 12/2009 | Snyder ......................... | 424/76.5 |
| 2010/0015081 | A1 * | 1/2010 | Drahos ........................ | 424/76.1 |
| 2010/0031450 | A1 * | 2/2010 | Wattebled et al. ............... | 8/137 |
| 2010/0093595 | A1 * | 4/2010 | Holzhauer ............... | C11D 1/83 510/342 |
| 2012/0100094 | A1 | 4/2012 | Reuter et al. | |
| 2012/0207699 | A1 * | 8/2012 | McHatton ............... | A61L 9/013 424/76.8 |

FOREIGN PATENT DOCUMENTS

WO WO2009/126473 A1 10/2009

OTHER PUBLICATIONS http://www.waterguru.net.au/products/MSB%20.pdf, BI-CHEM® MSB Multiple Spore Blend, Novozymes Biologicals, Inc., revised Oct. 21, 2002, (2 pages).

* cited by examiner

*Primary Examiner* — Lorna Douyon
(74) *Attorney, Agent, or Firm* — Maxwell J. Petersen; Lewis Brisbois Bisgaard & Smith

(57) ABSTRACT

A concentrated bioenzymatic cleaning product is provided which maintains a homogenous composition under static conditions and does not require shaking or mixing prior to dilution. The concentrated bioenzymatic cleaning product includes *bacillus* spores, a suspending and/or rheology modifying agent, an odor control agent, a pH adjuster, and water. The types and amounts of ingredients are selected to maintain the *bacillus* spores in suspension under static conditions, enabling the concentrated bioenzymatic cleaning product to be diluted using a proportioner system.

18 Claims, No Drawings

PROPORTIONER-READY BIOENZYMATIC CONCENTRATED CLEANING PRODUCT

CROSS REFERENCE TO RELATED APPLICATION

This application claims the benefit of U.S. Provisional Application No. 61/526,797 filed on 24 Aug. 2011. This Provisional Application is hereby incorporated by reference herein in its entirety and is made a part hereof, including but not limited to those portions which specifically appear hereinafter.

FIELD OF THE INVENTION

This invention is directed to a proportioner-ready bioenzymatic concentrated cleaning product that maintains a uniform composition under static conditions.

BACKGROUND OF THE INVENTION

Conventional bioenzymatic cleaning products contain active components which are composed of fine, insoluble spore particles that eventually settle under static conditions. In order to ensure homogeneity, the user is encouraged to shake or mix the product before use. These products can either be sold as ready-to-use products having the correct use composition, or as concentrates that are diluted prior to use.

Because of the tendency of the spore particles to settle, the concentrated products had to be shaken or mixed prior to dilution. The pre-mixing requirement rendered the concentrated products unsuitable for use with proportioner dispensing systems. The spore particles would need to be uniformly dispersed in the concentrated product before the concentrated product can be diluted and mixed with water using the proportioner.

There is a need or desire for a bioenzymatic concentrated cleaning products which maintains a uniform composition under static conditions, which can be diluted using proportioner dispensers.

SUMMARY OF THE INVENTION

The present invention is directed to a proportioner-ready bioenzymatic concentrated cleaning product that maintains a uniform composition under static conditions. The concentrated cleaning product does not settle, and does not require shaking or mixing prior to dilution. As such, the concentrated cleaning product is suitable for use in proportioner systems.

The bioenzymatic, concentrated cleaning product includes *bacillus* spores, a suspending and/or rheology modifying agent, an odor control agent, sufficient pH adjuster to maintain a pH of about 5.0 to about 9.5, and water. The type and amount of suspending agent are selected so that the *bacillus* spores remain suspended in the water under static conditions, and do not settle. This permanent suspension of *bacillus* spores enables the concentrate to be diluted using a proportioner system, and the concentrate does not require shaking or mixing prior to dilution.

The present invention is also directed to a method of preparing a bioenzymatic cleaning product from a concentrate. The method includes the steps of mixing about 5-55% by weight *bacillus* spores with a suspending and/or rheology modifying agent, an odor control agent, a pH adjuster and water, to form a concentrate in which the *bacillus* spores remain suspended in the water under static conditions. The concentrate is then diluted with water using a proportioner system, to yield the bioenzymatic cleaning product.

DETAILED DESCRIPTION OF THE INVENTION

The present invention is directed to a bioenzymatic, concentrated cleaning product that maintains a uniform composition under static conditions and does not require shaking or mixing to dilution. The concentrated cleaning product includes *bacillus* spores, a suspending agent, an odor control agent, a pH adjuster, and water. The specific types and amounts of the ingredients are selected such that the *bacillus* spores remain suspended in the water, and do not settle, under static conditions.

The *bacillus* spores are non-pathogenic spore-forming microorganisms that are capable of reacting with and removing various kinds of stains from carpets, fabrics, countertops, ceramic and metallic sinks and drains, and other surfaces and materials that become stained or soiled during use. Suitable *bacillus* spores are those that can produce extracellular enzymes that may include protease enzymes, urease enzymes, amylase enzymes, lypase enzymes, cellulase enzymes, and combinations thereof. The *bacillus* spores may constitute about 5-55% by weight, suitably about 10-35% by weight, of the bioenzymatic, concentrated cleaning product.

The *bacillus* spores may have an average particle diameter of about 2-50 microns, suitably about 10-45 microns. *Bacillus* spores are commercially available in blends in aqueous carriers, and are insoluble in the aqueous carriers. Suitable commercially available *bacillus* spore blends include without limitation Freshen Free™ CAN (10X), available from Novozymes Biologicals, Inc.; Genzyme® Renew Plus (10X), available from Genesis Biosciences, Inc.; and Genzyme® GT (10X, 20X and 110X), all available from Genesis Biosciences, Inc. In the foregoing list, the parenthetical notations (10X, 20X, and 110X) indicate relative concentrations of the *bacillus* spores.

The suspending and/or rheology modifying agent functions both to maintain the *bacillus* spores in suspension, and to make them resistant to agglomeration. Agglomeration of spores increases their effective particle size, making it more difficult to remain in suspension. The suspending and/or rheology modifying agent can function to suspend *bacillus* spore particles through the mechanism of producing high yield-stress fluids that have limited effect on viscosity, or through the mechanism of viscosity. In other words, the suspending and/or rheology modifying agent can either produce high performance at low viscosity, or can produce a high viscosity fluid that has high shear thinning properties, and is very pseudo-plastic or thixotropic. The suspending agents can be nonionic, cationic or anionic, and are suitably anionic.

Suitable anionic suspending and/or rheology modifying agents include without limitation xanthan gums, available from suppliers such as CP Kelco, Rhodia, TIC Gums, and R.T. Vanderbilt; guar gums, available from suppliers such as CP Kelco, Rhodia, and TIC Gums; acrylate copolymer rheology modifiers, such as Carbopol® rheology modifiers available from Lubrizol, Novethix® rheology modifiers available from Lubrizol, and Acusol™ and Acrysol™ rheology modifiers available from Dow Chemical Co.; poly (methylvinylether/maleic anhydride decadiene) crosspolymer, such as Stabileze® rheology modifiers available from International Specialty Products; and smectite clays, including magnesium aluminum silicates, also known as bentonite clays, available from R. T. Vanderbilt and Southern Clay Co. Nonionic suspending agents include without limitation cellulosics, such as carboxymethyl cellulose, hydroxyethyl cellulose, hydroxypropyl cellulose, hydroxypropylmethyl cellulose, methylcellulose, microfibrous cellulose, and chemically modified cellulose, available from CP Chemical, Ashland Chemical, and Dow Chemical. Combinations of the foregoing suspending and/or rheology modifying agents can also be employed.

The suspending and/or rheology modifying agent may constitute about 0.1-2.0% by weight of the bioenzymatic, concentrated cleaning product. The desired amount depends largely on the activity of the particular suspending agent. One suitable suspending agent, Kelzan® AP xanthan gum available from CP Kelco, is highly effective at a relatively low concentration of about 0.15% by weight. Smectite clays are less active, and are therefore more effective at higher concentrations.

The odor control agent can be a fragrance, a malodor control agent, or a combination thereof. Depending on the type of odor control agent and the end use application, the odor control agent may constitute about 0.1-2.0% by weight of the bioenzymatic, concentrated cleaning product. Suitable odor control agents include without limitation citrus and other fragrances, available from Oriental Aromatics and Belle-Aire Fragrances; Oreodone® malodor control agent, available from Belle-Aire Fragrances; Odor-Modifying Complex Technology ("OMC"), available from Belle-Aire Fragrances; Pro-Assure® malodor control agents, available from ProChem Specialties; zinc recinoleate, available from DeGussa; essential oils; and combinations thereof.

The purpose of the pH adjuster is to maintain the pH of the bioenzymatic, concentrated cleaning product within a range of about 5.0-9.5, suitably about 6.0-8.0. The *bacillus* spores are most effective for cleaning and stain removal within these ranges. Also, the ability of the *bacillus* spores to remain in suspension, and resist agglomeration and settling, is somewhat pH dependent. Suitable pH adjusters include organic acids, mineral acids, and combinations thereof. The suitable amount is whatever is effective to maintain the pH within the foregoing desired ranges. One particularly suitable pH adjuster is lactic acid. Purac®88 is an 88% active lactic acid available from Purac Biomaterials.

Optional additional ingredients can also be included in the bioenzymatic, concentrated cleaning product. These optional ingredients include without limitation wetting agents and dispersing agents. Wetting agents have a portion with an affinity for the surfaces of the *bacillus* spore particles, and a portion that is hydrophilic. The wetting agent ensures that the spore particles are thoroughly wetted by the solvent. Wetting agents are typically nonionic surfactants and can be aliphatic, aliphatic-silicon, or aliphatic-fluorine based. The wetting agents can constitute about 0.01-5.0% by weight of the bioenzymatic, concentrated cleaning product.

Dispersing agents enable the suspending agents to be more effective in keeping the *bacillus* spore particles uniformly suspended. They may be anionic, cationic, or amphoteric in nature. The dispersing agent attaches and/or associates with the surfaces of the *bacillus* spores, and the resulting surface charge causes the *bacillus* spores to repel each other. This repulsion both discourages agglomeration and helps keep the *bacillus* spores in suspension. The dispersing agent helps keep the wetted spore particles dispersed and mutually repulsed, and may be present at about 0.01-5% of the bio-enzymatic, concentrated cleaning product. Some wetting agents are also dispersing agents.

Water typically makes up the balance of the bioenzymatic, concentrated cleaning product. Water can be present in an amount of at least about 45% by weight, suitably of least about 50% by weight, or at least about 60% by weight. Most or all of the water can be provided by the commercially available *bacillus* spore blend, as described above.

The present invention also includes a method of preparing a bioenzymatic cleaning product using a concentrated bioenzymatic cleaning product, as described above. The method includes the steps of mixing about 5-55% weight *bacillus* spores with a suspending and/or rheology modifying agent, an odor control agent, sufficient pH adjuster to maintain a pH of about 5.0-9.5, and water, to form a concentrate (which is the concentrated, bioenzymatic cleaning product described above). The *bacillus* spores remain suspended in the concentrate under static condition, without shaking or mixing, and do not settle. The concentrate is then diluted with water using a proportioner system, to yield the bioenzymatic cleaning product. The dilution ratio may range from about 1 to 100 parts by weight water per part by weight concentrate, depending on the end use application and the composition of the concentrate.

EXAMPLE

A bioenzymatic, concentrated cleaning product was prepared having the following composition.

| Component (Trade Name) | Description | Supplier | Unit of Measure | Quantity (fraction %) | Function |
|---|---|---|---|---|---|
| Freshen Free CAN 10X Conc. | *Bacillus* Spore Blend composed of fine insoluble particles | Novozyme | LB | 0.9840 | Source of enzymatic cleaning & odor control agents |
| Kelzan AP | Xanthan Gum | CP Kelco | LB | 0.0015 | Suspending & Stablizing aid |
| Citrus Breeze | Fragrance and/or Malodor Control | Oriental Aromatics & Belle-Aire | LB | 0.0125 | Fragrance for appeal & Malodor control agent |
| Purac 88 (q.s.) Adjust pH to 7.0 | 88% active Lactic Acid | Purac | LB | 0.0010 | pH adjustment and corrosion control |
| Total = | | | LB | 1.000 | |

The ingredients were mixed together to form the bioenzymatic, concentrated cleaning product. The product can be placed in a transparent container and allowed to remain static for a time period of up to two years. The *bacillus* spores can remain in suspension during the entire period, with no settling observed. The stability can be adjusted to less than two years and only needs to be long enough for the concentrated cleaning product to remain in storage, and in the proportioner until exhausted, and a new container of concentrated cleaning product is inserted. If the replacement container has remained in storage beyond its designed stability time, the concentrated cleaning product can be re-suspended (such as by shaking) before being installed in the proportioner. The concentrated cleaning product will then remain in suspension for the longest projected time needed for complete use in the proportioner.

While the embodiments of the invention described herein are presently preferred, various modifications and improvements can be made without departing from the spirit and scope of the invention. The scope of the invention is defined by the appended claims, and all changes that fall with in the meaning and range of equivalents are intended to be embraced therein.

We claim:

1. A bioenzymatic, concentrated cleaning product, consisting essentially of:
   *bacillus* spores, having an average diameter of 5-50 microns and selected from the group consisting of extracellular protease enzymes, extracellular urease enzymes, extracellular amylase enzymes, extracellular lypase enzymes, extracellular cellulase enzymes, and combinations thereof;
   a suspending and/or rheology modifying agent;
   an odor control agent;
   sufficient pH adjuster to maintain a pH of 7.0 to about 9.5;
   optional wetting agents and dispersing agents; and
   a balance of water;
   wherein the *bacillus* spores are present at 15% to 55% by weight and are able to remain suspended in the water for two years under static conditions.

2. The bioenzymatic, concentrated cleaning product of claim 1, wherein the suspending and/or rheology modifying agent is selected from the group consisting of xanthan gum, guar gum, acrylate copolymers, celluloses, smectic clays, and combinations thereof.

3. The bioenzymatic, concentrated cleaning product of claim 1, wherein the suspending agent comprises xanthan gum.

4. The bioenzymatic, concentrated cleaning product of claim 1, wherein the suspending and/or rheology modifying agent is present at about 0.1-2% by weight.

5. The bioenzymatic, concentrated cleaning product of claim 1, wherein the odor control agent is selected from the group consisting of fragrances, malodor control agents, and combinations thereof.

6. The bioenzymatic, concentrated cleaning product of claim 1, wherein the odor control agent is present at about 0.1-2% by weight.

7. The bioenzymatic, concentrated cleaning product of claim 1, wherein the pH adjuster is selected from the group consisting of organic acids, mineral acids, and combinations thereof.

8. The bioenzymatic, concentrated cleaning product of claim 1, wherein the pH adjuster comprises lactic acid.

9. The bioenzymatic, concentrated cleaning product of claim 1, wherein the water is present in an amount of at least about 45% by weight.

10. A bioenzymatic, concentrated cleaning product, consisting essentially of:
    35% to 55% by weight *bacillus* spores having an average particle diameter of 5-50 microns;
    about 0.1-2% by weight of a suspending and/or rheology modifying agent;
    about 0.1-2% by weight of an odor control agent;
    an acidic pH adjuster
    optional wetting agents and dispersing agents; and
    a balance of water;
    wherein the *bacillus* spores are able to remain suspended in the water for two years under static conditions.

11. The bioenzymatic, concentrated cleaning product of claim 10, wherein the suspending agent comprises a gum.

12. The bioenzymatic, concentrated cleaning product of claim 10, wherein the odor control agent produces a citrus odor.

13. The bioenzymatic, concentrated cleaning product of claim 10, wherein the pH adjuster comprises sufficient acid to maintain a pH of about 5.0-9.5.

14. The bioenzymatic, concentrated cleaning product of claim 10, wherein the pH adjuster comprises sufficient acid to maintain a pH of about 6.0-8.0.

15. The bioenzymatic, concentrated cleaning product of claim 10, wherein the water is present in an amount of at least about 45% by weight.

16. A method of preparing a bioenzymatic cleaning product from a concentrate, consisting of the steps of:
    mixing 15% to 55% by weight *bacillus* spores having an average particle diameter of 5-50 microns with a suspending and/or rheology modifying agent, an odor control agent, sufficient pH adjuster to maintain a pH of about 5.0-9.5, optional wetting agents and dispersing agents, and a balance of water, to form a concentrate; and
    diluting the concentrate with water using a proportioner system, to yield the bioenzymatic cleaning product.

17. A bioenzymatic concentrated cleaning product from a concentrate, consisting essentially of:
    *bacillus* spores having an average particle diameter of 5-50 microns and selected from the group consisting of extracellular protease enzymes, extracellular urease enzymes, extracellular amylase enzymes, extracellular lipase enzymes, extracellular cellulose enzymes, and combinations thereof;
    a suspending and/or rheology modifying agent;
    an odor control agent:
    sufficient pH adjuster to maintain a pH of about 5.0 to about 9.5;
    optional wetting agents and dispersing agents; and
    a balance of water;
    wherein the *bacillus* spores are present at 35% to 55% b weight and are able to remain suspended in the water for two years under static conditions.

18. A bioenzymatic concentrated cleaning product, consisting of:
    *bacillus* spores having an average particle diameter of 5-50 microns and selected from the group consisting of extracellular protease enzymes, extracellular urease enzymes, extracellular amylase enzymes, extracellular lipase enzymes, extracellular cellulose enzymes, and combinations thereof;
    a suspending and/or rheology modifying agent;
    an odor control agent:
    sufficient pH adjuster to maintain a pH of about 5.0 to about 9.5;
    optional wetting agents and dispersing agents; and
    a balance of water.

* * * * *